(12) United States Patent
Royer et al.

(10) Patent No.: US 7,143,437 B2
(45) Date of Patent: Nov. 28, 2006

(54) SYSTEM AND USER INTERFACE FOR MANAGING USER ACCESS TO NETWORK COMPATIBLE APPLICATIONS

(75) Inventors: Barry Lynn Royer, Blue Bell, PA (US); John Andrew Heil, Malvern, PA (US)

(73) Assignee: Siemens Medical Solutions Health Services Corporation, Malvern, PA (US)

( * ) Notice: Subject to any disclaimer, the term of this patent is extended or adjusted under 35 U.S.C. 154(b) by 879 days.

(21) Appl. No.: 09/817,324

(22) Filed: Mar. 26, 2001

(65) Prior Publication Data

US 2002/0095605 A1 Jul. 18, 2002

Related U.S. Application Data

(60) Provisional application No. 60/261,148, filed on Jan. 12, 2001.

(51) Int. Cl.
*H04L 9/00* (2006.01)
*G06F 15/173* (2006.01)
*G06F 15/16* (2006.01)

(52) U.S. Cl. .......................... 726/8; 713/168; 726/21; 709/225; 709/229

(58) Field of Classification Search ................ 713/201, 713/202, 168; 709/217, 229, 225, 227; 707/10; 726/8, 5, 21
See application file for complete search history.

(56) References Cited

U.S. PATENT DOCUMENTS 5,657,480 A 8/1997 Jacobson .................... 395/555
5,708,780 A * 1/1998 Levergood et al. ......... 709/229
5,818,936 A 10/1998 Mashayekhi ................. 380/25
5,884,312 A * 3/1999 Dustan et al. ................ 707/10

(Continued)

FOREIGN PATENT DOCUMENTS

EP 0 718 784 A1 6/1996

(Continued)

OTHER PUBLICATIONS

RFC1738 Uniform Resource Locators (URL).

(Continued)

*Primary Examiner*—Emmanuel L. Moise
*Assistant Examiner*—Zachary A. Davis
(74) *Attorney, Agent, or Firm*—Alexander J. Burke

(57) ABSTRACT

A system and associated communication protocol facilitates management of user access to network (including Internet) compatible applications. An authentication system used by a first application for managing user access to at least one of a plurality of network compatible applications uses an authentication processor. The authentication processor receives user identification information including a user identifier and initiates authentication of the user identification information using an authentication service. The authentication system also includes a communication processor for communicating an authentication service identifier and a corresponding user identifier to a managing application. The authentication service identifier identifies an authentication service used to authenticate identification information of the corresponding user. The authentication processor maps a non-authenticated user identifier of a second application to an authenticated different user identifier of a first application using a database.

23 Claims, 10 Drawing Sheets

U.S. PATENT DOCUMENTS

| | | | | |
|---|---|---|---|---|
| 5,892,828 | A * | 4/1999 | Perlman | 713/183 |
| 5,892,905 | A | 4/1999 | Brandt et al. | 395/187.01 |
| 5,903,889 | A * | 5/1999 | de la Huerga et al. | 707/3 |
| 5,928,363 | A | 7/1999 | Ruvolo | 713/201 |
| 5,995,939 | A * | 11/1999 | Berman et al. | 705/3 |
| 6,014,702 | A | 1/2000 | King et al. | 709/227 |
| 6,049,877 | A * | 4/2000 | White | 713/201 |
| 6,052,785 | A | 4/2000 | Lin et al. | 713/201 |
| 6,065,120 | A | 5/2000 | Laursen et al. | 713/201 |
| 6,085,249 | A | 7/2000 | Wang et al. | 709/229 |
| 6,092,196 | A | 7/2000 | Reiche | 713/168 |
| 6,115,040 | A | 9/2000 | Bladow et al. | 345/335 |
| 6,128,738 | A | 10/2000 | Doyle et al. | 713/185 |
| 6,161,185 | A | 12/2000 | Guthrie et al. | 713/201 |
| 6,170,017 | B1 | 1/2001 | Dias et al. | 709/235 |
| 6,175,831 | B1 | 1/2001 | Weinreich et al. | 707/10 |
| 6,178,505 | B1 | 1/2001 | Schneider et al. | 713/168 |
| 6,178,511 | B1 * | 1/2001 | Cohen et al. | 713/201 |
| 6,185,567 | B1 | 2/2001 | Ratnaraj et al. | 707/10 |
| 6,557,039 | B1 * | 4/2003 | Leong et al. | 709/229 |
| 6,941,313 | B1 | 9/2005 | Seliger et al. | |
| 6,971,067 | B1 | 11/2005 | Karson et al. | |
| 6,993,656 | B1 | 1/2006 | Peyravian et al. | |
| 7,043,752 | B1 * | 5/2006 | Royer et al. | 726/8 |
| 7,103,666 | | * 9/2006 | Royer et al. | 709/227 |
| 2002/0107772 | A1 * | 8/2002 | Jain et al. | 705/37 |

FOREIGN PATENT DOCUMENTS

EP 0 817 445 A2 1/1998

OTHER PUBLICATIONS

Methods of Authentication (4 pages).
RSA unveils Web user.
KB LABS rfc1510 The Kerberos Network Authentication Service.
U.S. Appl. No. 09/817,322, filed Mar. 26, 2001, Barry Lynn Royer et al.
U.S. Appl. No. 09/817,311, filed Mar. 26, 2001, Barry Lynn Royer et al.
U.S. Appl. No. 09/817,320, filed Mar. 26, 2001, Barry Lynn Royer et al.
U.S. Appl. No. 09/817,323, filed Mar. 26, 2001, Barry Lynn Royer et al.
U.S. Appl. No. 09/817,321, filed Mar. 26, 2001, Barry Lynn Royer et al.
"Temporary Global Passwords," *IBM Technical Disclosure Bulletin*, Mar. 1993, vol. 36:3 451-454.
Press Releases http://www.semillion.com/news/D60221.html.

* cited by examiner

| NAME | IN/OUT | TYPE | DESCRIPTION |
|---|---|---|---|
| AuthServer | IN | STRING | AUTHENTICATING SERVICE NAME. THIS IDENTIFIES THE AUTHENTICATION SYSTEM (DATABASE) USED TO AUTHENTICATE THE USER. IT, ALONG WITH UserID MAY BE USED AS A KEY INTO A USER-MAPPING TOOL FOR MAPPING userIDs (FOR A GIVEN USER) ACROSS MULTIPLE SYSTEMS. |
| Language | IN | STRING | LANGUAGE AND COUNTRY IDENTIFICATION. THE INTERNET RFC 1766 (STANDARD FOR LANGUAGE CODES) IS TO BE USED. |
| LogoffURL | IN | STRING | URL USED TO REDIRECT THE USER TO A LOG-ON SCREEN WHEN A SESSION TIME-OUT HAS BEEN DETECTED. THE URL MUST BE FULLY QUALIFIED (NO RELATIVE ADDRESSING). |
| LogoffURL Target | IN | STRING | NAME OF FRAME TO BE TARGETED WHEN THE BROWSER IS REDIRECTED TO LogoffURL. |
| TIMEOUT | IN | INTEGER | SESSION YTIME-OUT IN SECONDS. IF OMITTED, TIMEOUT DEFAULTS TO 10 MINUTES |
| UserID | IN | STRING | USER IDENTIFICATION. THIS (ALONG WITH THE AuthServer PROPERTY) IS USED TO HELP IDENTIFY THE USER. THIS SHOULD BE THE UserID USED TO AUTHENTICATE THE USER. (SEE AuthServer). |
| SessID | OUT | STRING | UNIQUE SESSION IDENTIFIER ASSIGNED BY MANAGER 250 |
| SessionKey | OUT | STRING | KEY TO BE USED TO ENCRYPT AND DECRYPT URL DATA. |
| SMResult | OUT | INTEGER | RESULT OF REQUEST.<br>□ SUCCESS<br>□ FAILURE |

FIG. 5

| NAME | IN/OUT | TYPE | DESCRIPTION |
|---|---|---|---|
| SessID | IN | STRING | SESSION IDENTIFIER. |
| SMResult | OUT | INTEGER | RESULT OF REQUEST.<br>☐ SUCCESS<br>☐ FAILURE<br>☐ NOT FOUND |

FIG. 6

| NAME | IN/OUT | TYPE | DESCRIPTION |
|---|---|---|---|
| SessID | IN | STRING | SESSION IDENTIFIER. |
| AuthServer | IN | STRING | STRING USED TO IDENTIFY THE USER DATABASE TO WHICH THE UserID IS ASSOCIATED. |
| UserID | IN | STRING | THE USER IDENTIFIER. |
| SMResult | OUT | INTEGER | RESULT OF REQUEST.<br>☐ SUCCESS<br>☐ FAILURE<br>☐ NOT FOUND<br>☐ TIME-OUT |

FIG. 7

| NAME | IN/OUT | TYPE | DESCRIPTION |
|---|---|---|---|
| SessID | IN | STRING | SESSION IDENTIFIER. |
| AuthServer | IN | STRING | STRING USED TO IDENTIFY THE USER DATABASE TO WHICH THE UserID IS ASSOCIATED. |
| UserID | OUT | STRING | THE USER IDENTIFIER. |
| SMResult | OUT | INTEGER | RESULT OF REQUEST.<br>☐ SUCCESS<br>☐ FAILURE<br>☐ NOT FOUND<br>☐ TIME-OUT |

FIG. 8

| NAME | IN/OUT | TYPE | DESCRIPTION |
|---|---|---|---|
| SessID | IN | STRING | SESSION IDENTIFIER. |
| AuthServer | OUT | STRING | THIS IDENTIFIES THE AUTHENTICATION SYSTEM (DATABASE) USED TO AUTHENTICATE THE USER. |
| LANGUAGE | OUT | STRING | LANGUAGE AND COUNTRY IDENTIFICATION. THE INTERNET RFC 1766 (STANDARD FOR LANGUAGE CODES) IS TO BE USED. |
| LogoffURL | OUT | STRING | URL USED TO REDIRECT THE USER TO A LOG-ON SCREEN WHEN A SESSION TIME-OUT HAS BEEN DETECTED. THE URL IS FULLY QUALIFIED (NO RELATIVE ADDRESSING). IF BLANK, THE APPLICATION SHOULD RETURN A BLANK PAGE TO THE BROWSER. |
| LogoffURL Target | OUT | STRING | NAME OF FRAME TO BE TARGETED WHEN THE BROWSER IS REDIRECTED TO LogoffURL. IF BLANK, NO TARGET FRAME SHOULD BE SPECIFIED |
| TIMEOUT | OUT | INTEGER | SESSION TIME-OUT IN SECONDS. |
| UserID | OUT | STRING | USER IDENTIFICATION USED TO AUTHENTICATE THE USER. |
| SessionKey | OUT | STRING | KEY TO BE USED TO ENCRYPT AND DECRYPT URL DATA. |
| SMResult | OUT | INTEGER | RESULT OF REQUEST.<br>☐ SUCCESS<br>☐ FAILURE<br>☐ NOT FOUND<br>☐ TIME-OUT |

FIG. 9

| NAME | IN/OUT | TYPE | DESCRIPTION |
|---|---|---|---|
| SessID | IN | STRING | SESSION IDENTIFIER. |
| CallbackURL | IN | STRING | URL TO BE CONTACTED WHEN A SPECIFIED SESSION EVENT OCCURS. THIS CAN BE ANY VALID URL COMPLETE WITH PATH INFORMATION AND QUERY DATA. THE URL IS REFERENCED Y AS IT IS ENTERED IN THIS PROPERTY. NOTE: THE URL SPECIFIED HERE IS TO BE VALID IN THE NETWORK SEGMENT WHERE THE MANAGER THAT INVOKES THE CALLBACK OPERATES (NETWORK ADDRESS TRANSLATION MAY BE NECESSARY). |
| CallbackType | IN | INTEGER | TYPE OF EVENT THAT WILL TRIGGER THIS CALLBACK. ONLY SESSION TERMINATION EVENT IS CURRENTLY SUPPORTED. POSSIBLE VALUE ARE:<br>1 - END SESSION EVENT |
| SMResult | OUT | INTEGER | RESULT OF REQUEST<br>☐ SUCCESS<br>☐ FAILURE<br>☐ NOT FOUND<br>☐ TIME-OUT |

FIG. 10

| NAME | IN/OUT | TYPE | DESCRIPTION |
|---|---|---|---|
| SessID | IN | STRING | SESSION IDENTIFICATION |
| SMResult | OUT | INTEGER | RESULT OF REQUEST<br>☐ SUCCESS<br>☐ FAILURE<br>☐ NOT FOUND<br>☐ TIME-OUT |

FIG. 11

| NAME | IN/OUT | TYPE | DESCRIPTION |
|---|---|---|---|
| SessID | IN | STRING | SESSION IDENTIFIER. |
| ActivityInterval | OUT | INTEGER | SECONDS SINCE LAST ACTIVITY. |
| TIMEOUT | OUT | INTEGER | SESSION TIME-OUT IN SECONDS |
| SMResult | OUT | INTEGER | RESULT OF REQUEST.<br>☐ SUCCESS<br>☐ FAILURE<br>☐ NOT FOUND<br>☐ TIME-OUT |

FIG. 12

| NAME | IN/OUT | TYPE | DESCRIPTION |
|---|---|---|---|
| ClearText | IN | STRING | THE STRING TO BE ENCRYPTED. EXAMPLE STRING: GSMHASH=4326&pid=17388902&patname=smith |
| SessionKey | IN | STRING | THE SHARED ENCRYPTION KEY TO BE USED. THIS IS THE *SessionKey* VALUE RETRIEVED THROUGH THE MANAGER 250 *GetSession* METHOD. |
| CipherText | Out | STRING | THE ENCRYPTED STRING. THIS IS USED TO VALUE THE DATA ELEMENT *GSM*. THE STRING IS ENCODED IN MIME 64 ENCODING FORMAT. |
| SMResult | Out | INTEGER | RESULT OF REQUEST.<br>☐ SUCCESS<br>☐ FAILURE |

FIG. 13

| NAME | IN/OUT | TYPE | DESCRIPTION |
|---|---|---|---|
| CipherText | IN | STRING | THE ENCRYPTED STRING. THIS TYPICALLY COMES FROM THE DATA ELEMENT *GSM* AND IS IN MIME 64 ENCODING FORMAT. |
| SessionKey | IN | STRING | THE SHARED ENCRYPTION KEY TO BE USED. THIS IS THE *SessionKey* VALUE RETRIEVED THROUGH THE MANAGER 250 *GetSession* METHOD. |
| ClearText | OUT | STRING | THE RESULTING DECIPHERED STRING. |
| SMResult | OUT | INTEGER | RESULT OF REQUEST.<br>☐ SUCCESS<br>☐ FAILURE |

FIG. 14

| NAME | IN/OUT | TYPE | DESCRIPTION |
|---|---|---|---|
| ClearText | IN | STRING | THE STRING TO BE HASHED. |
| HASH | OUT | STRING | THE RESULTANT HASH VALUE. |
| SMResult | Out | INTEGER | RESULT OF REQUEST.<br>☐ SUCCESS<br>☐ FAILURE |

FIG. 15

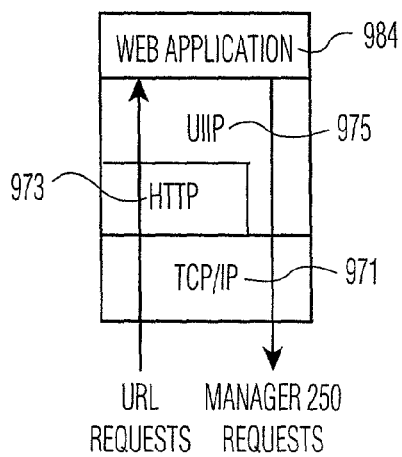

FIG. 16

SYSTEM AND USER INTERFACE FOR MANAGING USER ACCESS TO NETWORK COMPATIBLE APPLICATIONS

This is a non-provisional application of provisional application Ser. No. 60/261,148 by B. Royer filed Jan. 12, 2001.

BACKGROUND OF THE INVENTION

The management of information for medical purposes for use by physicians, hospital staff and other workers in the health care field poses a number of challenges. The information required by a physician, to optimize health care, is both varied in nature and in the sources from which it must be derived. A physician may typically need to have access to patient medical records, diagnostic images, diagnostic and dietary information systems, an appointment schedule, patient test results, medical literature, a prescription and drug interaction management system, insurance and billing information as well as a staff management system, for example. Access to such information and related services necessitate the use of a system including a communication platform supporting Internet operation and possibly local intra-net operation. Further, it is desirable that such a system for providing access to such an array of comprehensive information sources and related services should also provide a user interface that is suitable for use by a layman in the field and should not require extensive operator training.

There are a number of difficulties in providing such a comprehensive system. Specifically, it is necessary that such a system should support multiple different concurrent Internet based applications with the capability of conveying information between individual applications. These difficulties are compounded by the fact that individual applications may employ a unique data format or other operational feature limiting concurrent operation and interoperability. A system according to invention principles addresses these difficulties and derivative problems.

SUMMARY OF THE INVENTION

A system and associated communication protocol facilitates management of user access to network (including Internet) compatible applications. A managing application coordinates use of common, essential session properties to support user access capability. An authentication system used by a first application for managing user access to at least one of a plurality of network compatible applications uses an authentication processor. The authentication processor receives user identification information including a user identifier and initiates authentication of the user identification information using an authentication service. The authentication system also includes a communication processor for communicating an authentication service identifier and a corresponding user identifier to a managing application. The authentication service identifier identifies an authentication service used to authenticate identification information of the corresponding user.

In a feature of the invention, the authentication processor maps a non-authenticated user identifier of a second application to an authenticated different user identifier of a first application using a database.

BRIEF DESCRIPTION OF THE DRAWING

FIG. 5 shows the bidirectional command and response data communicated between an application and the managing application for initiating a session of user operation, according to invention principles.

FIG. 6 shows the bidirectional command and response data communicated between an application and the managing application for terminating a session of user operation, according to invention principles.

FIG. 7 shows the bidirectional command and response data used by an application for informing the managing application of a valid userid and associated authentication database, according to invention principles.

FIG. 8 shows the bidirectional command and response data used by an application to retrieve a valid userid for a particular authentication database from the managing application, according to invention principles.

FIG. 9 shows the bidirectional command and response data used by an application for retrieving session context data from the managing application, according to invention principles.

FIG. 10 shows the bidirectional command and response data used by an application to provide the managing application with a URL to be accessed upon an event terminating the current user operation session, according to invention principles.

FIG. 11 shows the bidirectional command and response data used by an application to inform the managing application of activity, according to invention principles.

FIG. 12 shows the bidirectional command and response data used by an application to retrieve its timeout status data held by the managing application, according to invention principles.

FIG. 13 shows the bidirectional command and response data used by an application to have a URL data string encrypted by the managing application, according to invention principles.

FIG. 14 shows the bidirectional command and response data used by an application to have a URL data string decrypted by the managing application, according to invention principles.

FIG. 15 shows the bidirectional command and response data used by an application to have a string hashed by the managing application, according to invention principles.

FIG. 16 is a system hierarchical protocol layer diagram including an interoperability protocol, according to the invention principles.

DETAILED DESCRIPTION OF PREFERRED EMBODIMENTS

A system and associated protocol enables Internet compatible applications comprising any grouping of software to be integrated into a workflow capable of supporting a browser. Workflow, as used in this document, refers to a task sequence typically involving initiation, intermediate command operation and termination of Internet compatible applications via a displayed user interface occurring between a user logon and a user logoff command. The system involves a centralized session manager and protocol for passing URL data between applications and other functions. These include providing services to coordinate user inactivity timeouts and provide common, essential session properties for facilitating concurrent application operation for providing access to an array of comprehensive (medical and other) information sources and related services. Internet compatible applications employing this system may be dynamically re-organized to implement different workflows or task sequences involving different operational constraints and limitations. The system advantageously facilitates reuse and interoperability of web based applications in multiple different sequences and concurrent operation configurations.

The system addresses a variety of problems involved in supporting concurrent operation of Internet compatible applications for accessing multiple information sources and related services for medical and other purposes. As such, the system addresses the problems involved in maintaining concurrent operation of applications in a framework providing a common web browser-like user interface. The system specifically addresses problems involved in managing different inactivity timeout periods and in facilitating user initiation (e.g., logon), operation and termination (e.g., logoff) of multiple Internet applications and in securely passing URL, patient (and user) identification and other information between applications. A managing application is employed to coordinate user operation sessions. Specifically the managing application coordinates inactivity timeout operation and maintains and conveys properties between concurrent applications in order to create a smooth user operation session. For this purpose, the managing application also coordinates the use of a single logon screen common to multiple concurrent applications.

The principles of the invention may be applied to any system involving concurrent operation of different software applications. Further, although the disclosed system is described in the context of communicating and processing web page data and associated URLs (Universal Resource Locators), this is exemplary only. The system may process any form of data that may be communicated via Internet Protocol (IP) or HyperText Transmission Protocol (HTTP) from an Internet source and includes any form of packetized data including streamed video or audio data, telephone messages, computer programs, Emails or other communications, for example.

Figure 1:
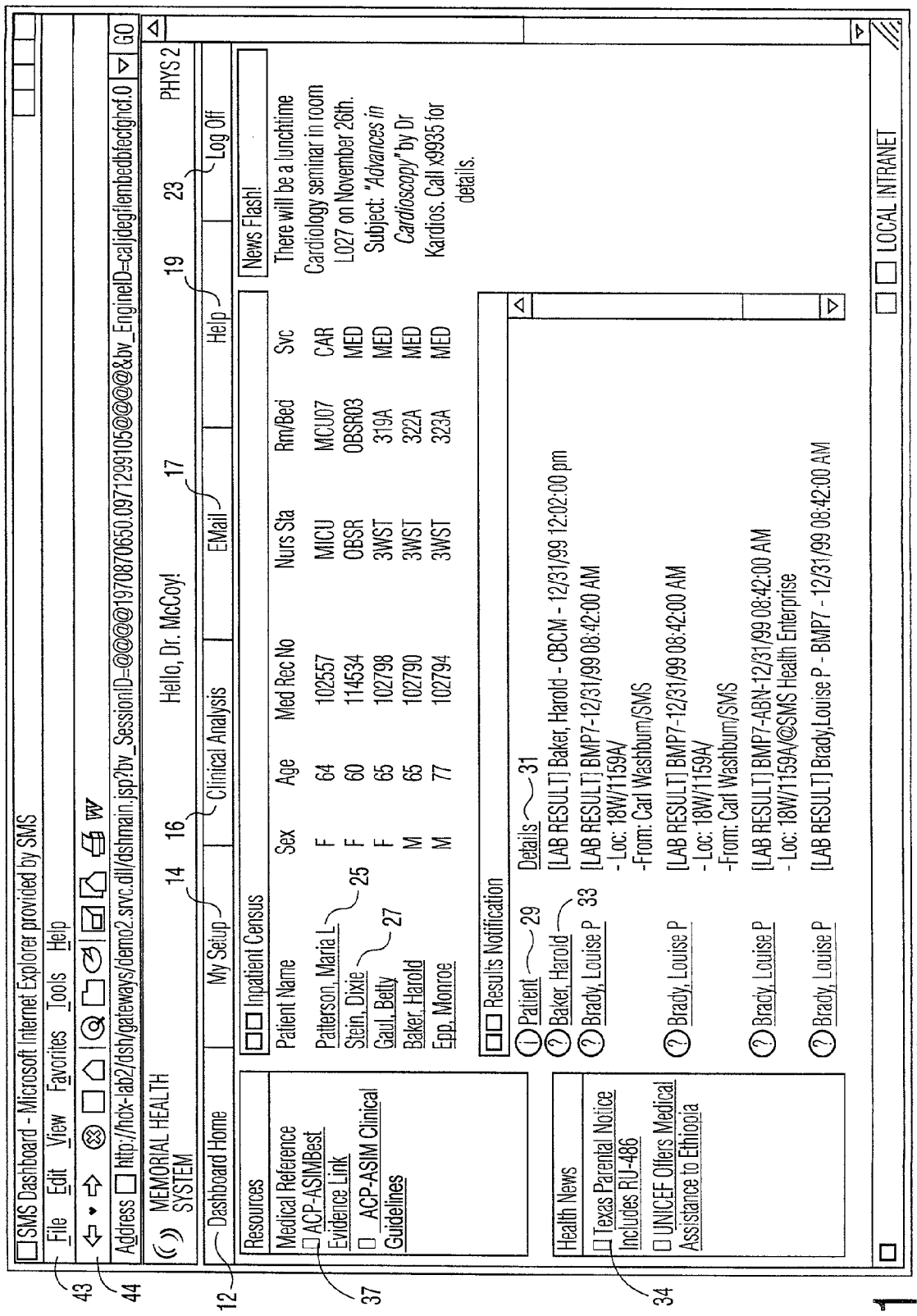
FIG. 1 shows a web browser window including multiple links to a plurality of medical related applications, according to invention principles.

FIG. 1 shows a web browser composite window 10 including multiple links to a plurality of medically related applications. The web browser provides typical command toolbars 43 and 44 as well as an application initiation bar (items 12–23). The web browser interface permits a user to initiate multiple concurrent applications including, for example, an application providing an inpatient census window (e.g. for patients 25 and 27) together with a laboratory test results application providing a results notification window including displayed items 29, 31 and 33. Other concurrent applications permit access to health care information and resources such as via reference link 37 and news item link 34.

Figure 2:
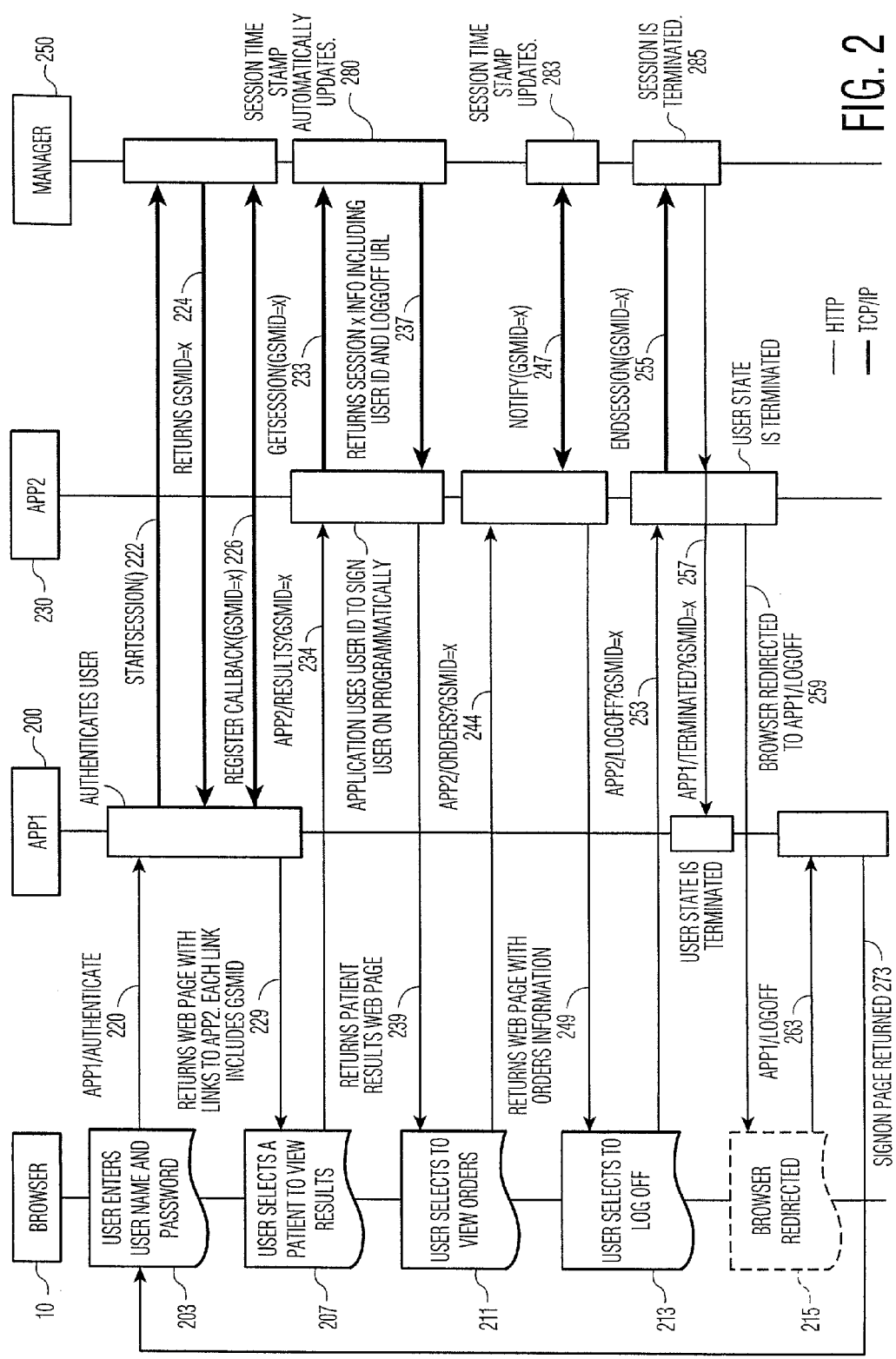
FIG. 2 is a system command flow diagram showing system protocol operation involving a managing application (GSM—Global Session Manager) two applications and a web browser, according to the present invention.

FIG. 2 is a system command flow diagram showing system protocol operation involving a managing application 250 (GSM—Global Session Manager), two applications 200 and 230 (App1 and App2) and a web browser 10 (e.g. as described in connection with FIG. 1). The system protocol employed by manager 250 supports coherent harmonized and concurrent operation of multiple applications (e.g., applications 200 and 230) in implementing a task sequence or workflow. Manager 250 is advantageously used by the applications 200 and 230 to reference global data that is essential to a workflow. Such global data includes, for example, user identification information, a shared key used for the encryption of URL data, and a common URL to be used for handling a logoff and logon function. The system protocol involves applications 200 and 230 intermittently notifying manager 250 of activity to prevent an inactivity timeout while a user is active in another concurrent application.

Manager 250 employs a system protocol for passing session context information to applications 200 and 230 via URL query or form data. The session context information comprises a session identifier, a hash value, and application specific data. The session identifier is used by applications 200 and 230 to identify a user initiated session in communicating with manager 250. The hash value is used by applications 200 and 230 to validate that a received URL has not been corrupted, intentionally or otherwise. The application data portion of the session context information may or may not be encrypted as determined by the application communicating the URL. The application specific data is tailored to meet the intended function of a target application. The protocol employed by manager 250 supports applications that use the generated session context information and do not alter it. In alternative embodiments, applications 200 and 230 may employ internal managers using other protocols to support a global context concept, either as an alternative to manager 250, or in addition to manager 250. Such other protocols comprise, for example, HL7 (Health Level Seven) protocol or CCOW (Clinical Context Object Workgroup V1.2 Ratified May 2000) protocol. The described system supports use of alternative protocols as well as the communication of data between applications, other than just session context information.

Manager 250 maintains security by operating in a secure environment that prevents unauthorized access to the manager application itself. Security is also provided by ensuring applications 200 and 230 (that communicate with manager 250) also operate in a secure environment. Manager 250 also maintains security by detecting and ignoring received URLs that have been intentionally or otherwise corrupted and by preventing replay and display of received URLs.

Figure 4:
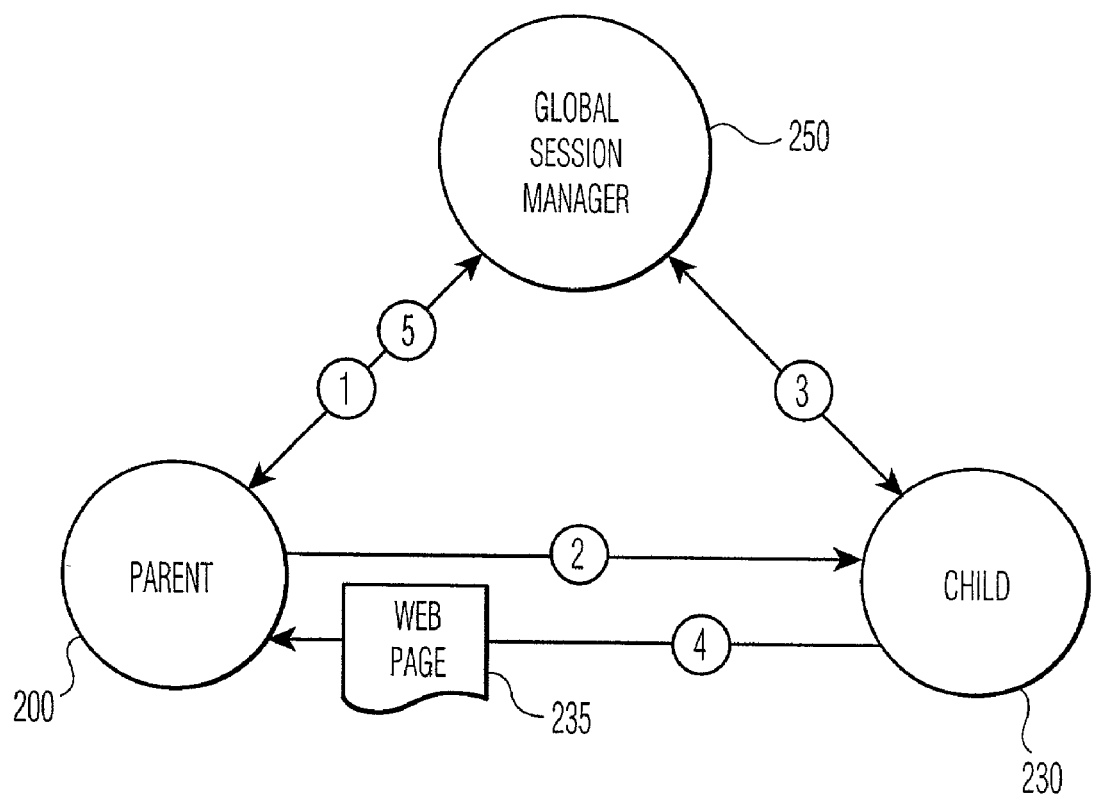
FIG. 4 shows command interaction between multiple concurrently operating applications, according to invention principles.

FIG. 4 shows command interaction between concurrently operating applications 200 and 230, web browser 235 and manager 250 using a system interoperability protocol in accordance with invention principles. FIG. 4 shows a simplified version of the command interaction of FIG. 2. In an exemplary user operation session, parent application 200 starts a session and notifies manager 250 of activity (1). Subsequently, parent application 200 references a child application 230 (2). A child application typically provide web pages to other applications. Specifically, child application 230 notifies manager 250 of activity (3) and returns a web page 235 to parent application 200 (4). Eventually, parent application 200 terminates the session via a command to manager 250 (5). The application that establishes a session with manager 250 is said to be the parent application. All additional applications that participate in that session are referred to as child applications. The collection of the parent and all child applications together are said to be the participants. Manager 250 provides centralized services to the parent and child applications in order to coordinate them. A parent application creates a session after the user is authenticated and before a child application is referenced. A parent application may delay establishing a session until a specific event, e.g., until the parent downloads (to a browser) a web page containing links to child applications. Typically, a session is ended when the user signs off or when the user times out due to inactivity.

Returning to FIG. 2, a command 220 to initiate parent application 200 and to authenticate user identification information (password and user name entered via browser command 203) is passed via browser 10 to parent application 200. Parent application 200 authenticates the received user information using either an internal or external database of authentication information for verification. Upon successful authentication, parent 200 communicates startsession 222 data (as shown in FIG. 5) to manager 250 to establish a new session. The startsession command is invoked prior to generating links to another application. FIG. 5 shows the startsession bidirectional command and response data communicated between parent application 200 and manager 250 for initiating a session of user operation. Parent 200 determines the FIG. 5 properties comprising authserver 500, language 503, logoffurl 505, logoffurltarget 507, timeout 513 and userid 517. In response, manager 250 returns properties (in command 224 of FIG. 2) to parent 200 comprising, a unique session identifier 520 to be used when referencing child application URLs and manager 250, session key 530 (used to encrypt and decrypt URL data) and SMResult 525 indicating command status. A failure indication by SMResult 525 indicates that the service is unavailable possibly due to a temporary condition (e.g. network problems) or to a permanent condition (e.g. a configuration error). None of the FIG. 5 properties are mandatory. In an alternative embodiment, manager 250 returns session identifier 520 in encrypted form for decryption and use by application 200 using a predetermined encryption key available to applications including applications 200 and 230 and manager 250.

Through the startsession command, parent 200 sets static session properties that are to be used by all participants of the session. This, in affect, means that parent application 200 sets the tone and control of the user experience. For example, the parent determines the logon/logoff web page to be used and how the user is known to the participants as well as the user inactivity limits. It is the responsibility of parent application 200 to ensure that proper authentication has been carried out before it creates a session.

In the command interaction diagram of FIG. 2, parent application 200 registers a URL with manager 250 using a register callback command (indicated as item 226 in FIG. 2 and detailed in FIG. 10). Specifically, parent 200 provides manager 250 with a callback URL (Universal Resource Locator 450 in FIG. 10) defining a web page to be accessed upon an event terminating the current user operation session. The callback URL is provided to manager 250 together with session identifier 449 and callback type indicator 453 (FIG. 10). The register callback command is also employed by manager 250 to update an activity status time indicator used to monitor parent application 200 activity status. In response to the register callback command, manager 250 returns a command status indicator (SMResult 445 of FIG. 10 indicated by item 226 of FIG. 2) to parent 200. Indicator 445 indicates status such as command success, failure, time out or a not found condition. A failure result indicates that the service is unavailable possibly due to a temporary condition (e.g. network problems) or to a permanent condition (e.g. a configuration error). A time out condition indicates that the session has timed out and parent application 200 redirects browser 10 to the URL found in the logoffurl property targeted to the frame found in the logoffurltarget property (items 505 and 507 of FIG. 5). A not found condition indicates that manager 250 has no record of the requested session ID. In response, parent application 200 displays a message indicating that the session is no longer active and that the user should navigate to the logon screen to restart.

In the command interaction diagram of FIG. 2, parent application 200, in command 229, returns a web page to browser application 10 following register callback command (226). The web page includes embedded URL links to other (child) applications including a URL link to (child) application 230. The embedded URL links are processed, to include within the URL data itself, the session identifier and additional context information if required (e.g., a patient identifier). Application 230 uses the session identifier in communicating with managing application 250 in order to obtain information about the session for facilitating user operation and task workflow. Manager 250 identifies an authenticated user of child application 230 from previously stored identification data eliminating the need for a user to logon again to access child application 230. This constitutes a silent logon process. A child application providing access to other child applications generates URL links (to the other child applications) incorporating the session identifier and additional context information as required. A parent or child application providing access to its own web pages may optionally pass the session identifier or context via a URL. An application creates a session via a startsession command when, for example, it create a URL reference to a different application and a session identifier has not yet been established. If a session identifier has already been established and provided to the application, it is used and propagated when referencing other applications.

The maintenance of security is an important consideration in processing the embedded URL links for incorporation in the web page returned to browser 10 in command 229 of FIG. 2. Also, different security concerns are involved in processing URL links to include the session identifier and additional context information. One concern is the prevention of unauthorized access to manager 250. Other concerns include the prevention of URL replay once a session has ended and provision of protection against attacks involving corruption of URL data.

The prevention of unauthorized access to manager 250 is facilitated by ensuring that applications 200 and 230 that access manager 250 operate in a protected and trusted environment. This is attained by operating the system on proprietary networks (e.g. Wide Area Networks—WANs or Local Area Networks—LANs) and intra-nets. Applications that are accessed through public networks such as the Internet are designed so that components accessing manager 250 operate in a trusted environment. Additional levels of security are attainable by employing additional protocol layers, e.g., involving digitally signed software, user certificates, or SSL (Secure Sockets Layer V3.0) protocol of November 1996 by Internet Engineering Task Force (IETF), etc.

The prevention of URL replay and protection against URL corruption (deliberate or otherwise) is advantageously achieved by the use of strong encryption, as well as limited duration sessions and randomly generated shared encryption keys. These security measures ensure that URL query or form data is unaltered and that a link generated by a participant application (e.g., applications 200 and 230) is not redirected. The security measures also ensure that a valid URL is not replayed after a session has ended and that a session identifier is difficult for an unauthorized party to determine.

The creation of a session, e.g., via startsession command 226 of FIG. 2, initiates the generation of an encryption key (530 of FIG. 5) for that session by manager 250 that is returned to application 200 by command 224 of FIG. 2. This key is generated on a random basis and is shared for the duration of that session with those applications that are participants of the session (applications 200 and 230 in the example of FIG. 2). The key is used by an encryption algorithm employed by application 200 to encrypt the query or form data portions of a generated URL link (e.g. a URL link to child application 230) that is incorporated in a web page provided by command 229 for display using browser 10. The encryption method is designed so that if any of the encrypted string is changed, it prevents the string from being successfully decrypted. In addition, manager 250 uses a unique session identifier (SID—item 520 of FIG. 5) for each new session. This procedure protects against the corruption and replay of a URL (once the session has ended) and prevents the generation of valid URL data from anywhere but participant applications.

In addition, application 200 ensures that a URL link (e.g. a URL link to child application 230) embedded in a web page provided for display using browser 10 is not redirected. For this purpose, application 200 generates a hash value from the domain, path, program, and program data portion of the URL. Application 200 (as the sending application) generates a hash value from the fully qualified URL link. Specifically, application 200 generates the hash value from the URL data either lying between the "http://" and the question mark "?" or from the data lying between the "http://" and the pound/number sign "#"—whichever comes first. The data used to create the hash value is the fully qualified URL even if relative addressing is used in the actual reference (e.g. in the HREF or ACTION attributes). In addition, the string to be hashed is advantageously converted to lower case before being hashed. This is done since it is recognized by the inventors that some web servers and browsers may not preserve case or may be sensitive to case. Further, the hash algorithm used in both the sending application 200 and receiving application 230 in this described embodiment is the RSA MD5 128 bit hashing algorithm. The RSA MD5 algorithm is the Rivest Shamir Adleman public key cryptosystem used with MD5 hash function and is described in publications available on the Internet. However, this is exemplary only and other algorithms or other mechanisms performing a function similar to that of the hashing function may also be employed. The created hash value is conveyed as part of the embedded URL link referencing child application 230 in the web page data provided by application 200 to browser 10.

In another embodiment, application 200 does not create the hash value itself but uses manager 250 to create the hashed value. Specifically, application 200 communicates with manager 250 using the bidirectional command and response data of FIG. 15 to have a string hashed. Application 200 sends the string to be hashed 783 (FIG. 15) to manager 250 which responds with the hashed value 787 and the status of this command (SMResult 789) indicating command success or failure.

Upon user selection of the embedded URL link via browser 10, the URL data and hash value are passed to application 230 via command 234. A user selects the embedded URL link (browser command 207) on browser 10 to view a patient laboratory results, for example. Application 230 decrypts the received hash value for comparison with a corresponding hash value independently generated from corresponding URL data retrieved from a web server. The corresponding URL data indicates the true URL link data and is therefore usable for verification. Application 230 independently generates a hash value from corresponding URL data comprising a concatenation of the following HTTP server-side attributes (or equivalents). For ASP applications (ASP means Active Server Page—a Microsoft proprietary style of processing web requests) the SERVER_NAME and SCRIPT_NAME are used. For non-ASP applications, e.g. for CGI (Common Gateway Interface) compatible applications the SERVER_NAME, SCRIPT_ NAME, and PATH_INFO are used. The independently generated hash value and the hash value received by application 230 from application 200 via browser 10 are compared and if they are not equal, the request to initiate application 230 is rejected.

Applications are vulnerable to the corruption of URL data and the context information conveyed within the URL data. The URL data conveyed from application 200 to application 230 includes context information comprising a session identifier and optionally a user or patient identifier. This URL data is potentially vulnerable to corruption to cause URL replay or redirection of an application to a substitute address or to gain access to application functions and parameters for unauthorized purposes. In order to protect against such corruption and to ensure that the entity being accessed is the one originally targeted, portions of the URL data conveyed between applications are advantageously encrypted.

Application 200 processes a URL for incorporation within web page data for communication to browser 10 and for communication to application 230 by concatenating the URL fields into one string prior to encryption using a key previously received from manager 250. The processed URL data includes a session identifier and encrypted data. A processed URL includes a field labeled as a GSM data field. The format of the field is as follows:

GSM=x:y

Where:
  GSM—is the key name of the "key=value" pair
  x—is the manager 250 session identifier
  :—is the field separator
  y—is the encrypted string The session identifier (x) is the session identifier (item 520 of FIG. 5) provided by manager 250 in the startsession command response 224 (FIG. 2). In its unencrypted form, the encrypted string (y) is itself made up of "key=value" pairs. A URL hash value (identified in a URL by the label GSH) is incorporated in a processed URL and is generated by hashing on the addressable portion of a fully qualified URL. The addressable portion of the URL is hashed to compress and reduce the quantity of data to be processed. Other x:y data field pairs may be included to accommodate requirements of particular applications and other application data may also be conveyed with a URL. However this other data is not encrypted within the GSM data field. Application data that is to be encrypted with the encryption key from manager 250 is placed into the encrypted portion of the GSM data field. The GSM data field is compatible with the Uniform Resource Identifiers (URI) syntax authored by the Internet Engineering Task Force (IETF) in Request for Comment document RFC 2396. The RFC documents are available via the Internet and are prepared by Internet standards working groups.

The URL processing performed by application 200 (and performed by other applications passing context data) is illustrated below.

An exemplary URL string that is to be processed is, www.smed.com/altoona/prd/results.exe/1?GSM=
        16253384937&GSH=24017&Pid=1772693&Frgclr=blue The data field GSM is the session identifier provided by manager 250. The data field GSH is the hash value derived by application 200. The derived hash value is advantageously encrypted by application 200 prior to its communication within processed URL data to other applications (e.g. application 230). Additionally, in this example application 200 encrypts a patient identifier (Pid) for communication to application 230. The system protocol employed by manager 250 (and applications 200 and 230) determines that data to be encrypted is collated into an individual MIME (Multipurpose Internet Mail Extension) format data field for encryption into one string. Therefore, as an example, the string GSH=24017&Pid=1772693 is encrypted into the string

16sfdjwhejeyw7rh3hekw

Application 200 encrypts the string using a two-key triple DES (Data Encryption Standard) algorithm in cipher block chaining mode employing a 64 bit block and an effective 112 bit key length. The resulting cipher text complies with the URL query data encoding format and represents a single value of a "key=value" pair. Although in this embodiment application 200 performs the encryption, in an alternative embodiment application 200 (or a child application) instructs manager 250 to perform the encryption. For this purpose, application 200 uses the bidirectional command and response data of FIG. 13 to have a URL data string encrypted into a MIME formatted string by manager 250.

In the embodiment in which the string is encrypted by manager 250, application 200 sends the string to be encrypted cleartext 653 together with the encryption key to be used, sessionkey 656 (FIG. 13), to manager 250. Manager 250 encrypts string 653 using key 656 and responds to application 200 with the encrypted string ciphertext 659 and command status indicator SMResult 664. SMResult 664 indicates command success or failure in a similar fashion to that previously described in connection with command 226, for example.

The session identifier and the encrypted text are concatenated into one field (per the manager 250 protocol) and the resulting processed URL data is:

www.smed.com/altoona/prd/results.exe/1?GSM=162
      53384937:16sfdjwhejey w7rh3hekw&Frgclr=
      blue Application 230 decrypts the encrypted portion of the processed URL data to provide the hash value for use in validating that application 230 is the intended recipient of the URL request. Application 230 compares the hash value received in the URL data with a corresponding hash value independently generated from corresponding URL data retrieved from a web server. If the two hash values do not match, the addressable portion of the URL has been altered and the request is rejected. In addition, application 230 rejects received URL data that does not contain at least an encrypted GSH portion. In other embodiments the context data (session identifier and patient identifier) may not be encrypted or may be conveyed within URL data in both encrypted and non-encrypted form. In the latter case, an application automatically parses received URL data to identify encrypted data elements and uses the encrypted data elements in preference to corresponding non-encrypted versions of the data elements. Further, although this example shows context and security data being passed as URL query data, this is exemplary only. The context and security (and other) data may be passed in another format, for example, the "GSM=value" data may be conveyed as form data via a Form and POST method. The Form and POST method is known in the art. Further, the URL processing functions described herein may also be employed by a browser application or a managing application in other embodiments.

Although in this embodiment application 230 decrypts the encrypted portion of the processed URL data to provide the hash value, in an alternative embodiment application 230 (or another parent or child application) instructs manager 250 to perform the decryption. For this purpose, application 230 uses the bidirectional command and response data of FIG. 14 to have an encrypted URL (MIME formatted) data string decrypted by manager 250. For this purpose, application 230 sends the string to be decrypted ciphertext 751 together with the encryption key to be used, sessionkey 753 (FIG. 14), to manager 250. Manager 250 decrypts encrypted string 751 using key 753 and responds to application 230 with the decrypted string cleartext 755 and command status indicator SMResult 757. SMResult 757 indicates command success or failure in a similar fashion to that previously described in connection with command 226, for example.

Upon successful validation of the received hash value following command 234 (FIG. 2) to initiate application 230, application 230 communicates with manager 250 via command 233 to obtain session context information. Specifically, application 230 employs the bidirectional command and response data of FIG. 9 to retrieve session context data from manager 250. Application 230 sends session identifier 900 (FIG. 9) to manager 250 in command 233. Manager 250 responds in command 237 with FIG. 9 properties comprising authserver 903, language 907, logoffurl 911, logoffurltarget 913, timeout 915 and userid 917, session key 921 and SMResult 923. These properties have a similar function as the corresponding properties previously described in connection with FIG. 5. Further, manager 250 (in step 280 of FIG. 2) updates a session activity time stamp maintained for application 230 and used to monitor application 230 activity in response to successful execution of commands 233 and 237 to retrieve session context information.

SMResult 923 is a status indicator that indicates command success, failure, time out or a not found condition. A failure result indicates that the service is unavailable possibly due to a temporary condition (e.g. network problems) or to a permanent condition (e.g. a configuration error). A time out condition indicates that the session has timed out resulting in manager 250 returning to application 230 the logoffurl property targeted to the frame found in the logoffurltarget property (items 911 and 913 of FIG. 9). In this condition the other property values are not valued and application 230 redirects browser 10 to the URL found in the logoffurl property targeted to the frame found in the logoffurltarget property. A not found condition indicates that manager 250 has no record of the requested session identifier. In response, application 230 displays a message indicating that the session is no longer active and that the user should navigate to the logon screen to restart.

Application 230, in command 239, returns a web page including patient laboratory results (previously requested via browser command 207) for display via browser application 10. The laboratory results web page incorporates an embedded link to view a web page provided by the same application (application 230) displaying a list of orders for laboratory tests. Therefore, the user selection of the embedded link to view laboratory test orders in browser command 211 represents an intra-application command request. Further, because the link to the test results page is an intra-application link there is no requirement for this particular embedded link to be processed in the manner previously described to incorporate the session identifier and other context information. Application 230 may employ its own mechanism for maintaining state between intra-application URL link selection and the provision of associated web pages. Alternatively, application 230 may optionally process the embedded intra-application URL link, in the manner previously described, in order to convey session identification and other context information between the different intra-application web page access states.

Application 230, in command 247, notifies manager 250 of activity using the bidirectional command and response data of FIG. 11 and in response (in step 283 of FIG. 2) manager 250 updates an inactivity timing status indicator maintained for application 230. Command 247 in FIG. 2 is representative only and in practice notification commands are advantageously repeated until the session is ended in order to prevent an application timing out due to inactivity. In other embodiments application 230 may use different schemes for notification. However, it is the responsibility of application 230 (or other participant applications including parent application 200) to notify manager 250 of activity in such a manner as to keep a session from timing out provided that the application is active. Application 230 sends session identifier 460 (FIG. 11) to manager 250 in command 247. Manager 250 responds in command 247 with a command status indicator SMResult 463 indicating success, failure, not found or time-out in a similar fashion to that previously described in connection with command 237, for example.

Application 230 may perform notifications using the command of FIG. 11 when it is called upon (e.g. when a web page is provided) or application 230 may notify manager 250 of activity using batched notification commands. Such a batched notification may be advantageously used in the case of a PC application that monitors key and mouse movements and periodically notifies manager 250 with a single notification, for example. The command of FIG. 11 is used by either a parent application or a child application in order to update activity status and, in response, manager 250 records the time at which it was notified. In addition, other commands may be used to notify manager 250 of activity. Specifically in this embodiment the commands depicted in FIGS. 9 and 10 (corresponding to commands 233 and 226 of FIG. 2 respectively) are used to notify manager 250 of activity.

In the described system, manager 250 acts as a central coordinator for monitoring activity of participant applications by requiring that participant applications notify manager 250 of activity. Participant applications may also query manager 250 in order to determine if a session is still active. This coordination and management function advantageously addresses problems involved in managing disparate inactivity time-out limits when different applications are combined into a single user task sequence and workflow. For example, such a problem arises if a user works in one application for a period of sufficient duration to trigger a time-out in another concurrent application. This situation leads to a loss of context and a confusing workflow.

Manager 250 is essentially passive in this embodiment and does not automatically generate a timeout event. Manager 250 maintains a time stamp for a session indicating when the session last had activity reported and initiates termination of a session if a session having an expired time stamp is referenced (e.g., via command 233) or if a session termination command is received. Upon termination of a session, manager 250 informs those participant applications of the termination that have previously requested a notification of session termination. In other embodiments, manager 250 may be configured to automatically generate a timeout event upon one or more predetermined conditions or combination of conditions.

In addition, an application (e.g. applications 200 or 230) uses the bidirectional command and response data format of FIG. 12 to retrieve its timeout status data maintained by manager 250. An application sends session identifier 573 (FIG. 12) to manager 250 and manager 250 responds with activityinterval 577, timeout indicator 583 and SMResult 589. The activityinterval 577 indicates the number of seconds since the last activity update, timeout indicator 583 identifies the time-out limit in seconds and status indicator SMResult 589 indicates command status. SMResult 589 indicates success, failure, not found or time-out in a similar fashion to that previously described in connection with command 237, for example.

Application 230, in command 249, returns a web page including laboratory test orders (previously requested via browser command 211) for display via browser application 10. Subsequently, the user elects to logoff via browser command 213 and in response browser 10 issues a logoff command 253 to application 230. Application 230, in command 255, instructs manager 250 that the session of user operation is to be terminated using the bidirectional command and response data of FIG. 6. Specifically, application 230 sends session identifier 600 (FIG. 6) to manager 250 in command 255 and in response (in step 285 of FIG. 2), manager 250 updates status indicators it maintains to reflect that session 600 is terminated. Manager 250 also responds to application 200 and to application 230 in command 257 with a command status indicator SMResult 603 identifying that the session is terminated and indicating status of the session termination command request. Specifically, SMResult 603 indicates success, failure, not found or time-out in a similar fashion to that previously described in connection with command 237, for example. However, applications receiving SMResult 603 assume the session is terminated irrespective of the nominal SMResult 603 status.

Upon receipt of SMResult 603 from manager 250, application 230 in command 259 redirects browser 10 (command 215) to access a logon web page available via the logoffurl property targeted to the frame found in the logoffurltarget property previously obtained from manager 250 in command 237. Specifically, browser 10 accesses a logon page at the logoffurl provided by parent application 200 via command 263 and this logon page is returned to browser 10 in command 273.

Manager 250 may also be instructed to terminate a session under conditions other than in response to a user initiated logoff command. Such conditions occur, for example, when (a) an inactivity time out limit is exceeded and (b) an application becomes non-responsive to manager 250 initiated polling. Such polling is initiated by manager 250 periodically to clean up a session operation and to eliminate non-responsive applications that have avoided inactivity time out through a software error or other occurrence.

Figure 3:
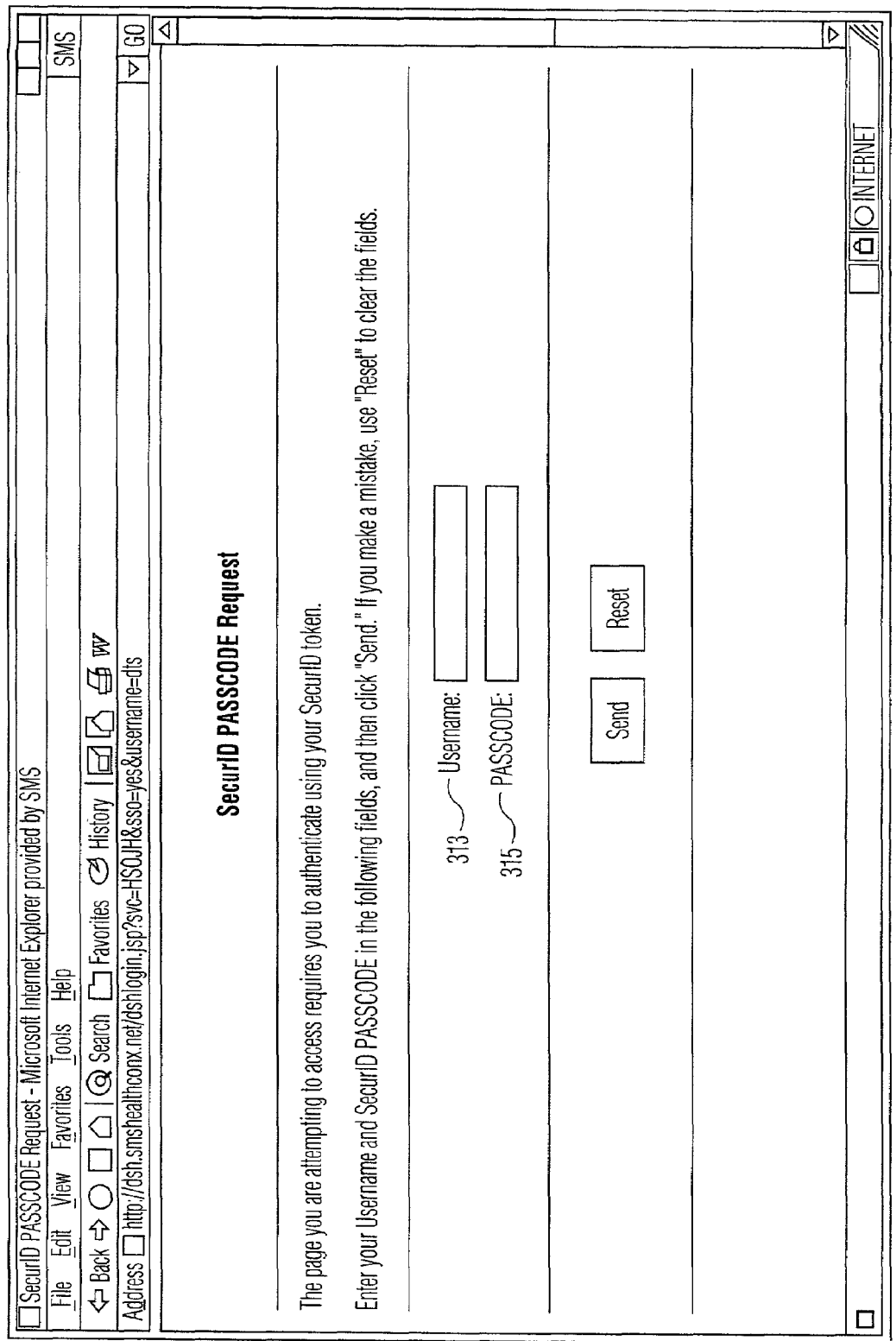
FIG. 3 shows a common logon menu used for multiple applications, according to invention principles.

FIG. 3 shows a common logon menu web page 310, supporting entry of username 313 and password 315, and enabling a single logon to provide access to multiple applications facilitating smooth workflow operation for a user. This is achieved by providing a logon menu web page as a common starting place to which a user is directed upon initial logon or upon logoff from a session of activity or upon a termination condition such as an error condition or upon time-out due to inactivity. For this purpose, manager 250 maintains a logoffurl property (e.g. item 505 of FIG. 5) provided by a parent application (e.g. application 200) that is used by participant applications to get back to a common starting web page. Upon a participant application receiving a time-out status from manager 250 or when manager 250 explicitly ends a session, a browser (e.g., browser 10 of FIG. 2) is redirected to the logon page at the URL specified in the logoffurl property maintained by manager 250.

A number of problems involved in providing a common logon web page are advantageously recognized. Specifically, problems are involved in enabling a user to logon once to access different applications with different user identifiers and different authentication systems. These problems are addressed in the present system by providing participant applications of a session with a list of AuthenticatingSystem-user ID pairs. A parent application (application 200) provides an authenticating service identifier and user identifier used by the parent application to authenticate the user via the authserver and userID properties (items 500 and 517 respectively) of the session initiation command of FIG. 5. This information is provided for use by participant applications to identify the parent application and to identify how the user is known by the parent application if necessary.

A participant application (parent or child) may also use the bidirectional command and response data of FIG. 7 to inform manager 250 of a valid userid and associated authentication database in a user operation session. Thereby, manager 250 compiles a database for mapping a userid of a participant application to an authenticated and different userid of a second application. This enables the second application to be accessed transparently to a user without the need for a user to re-login. An application (e.g., application 200 of FIG. 2) sends session identifier 700 (FIG. 7), authserver 703 and userid 705 to manager 250. Authserver 703 identifies the user authentication database associated with userid 705. Thereby, manager 250 compiles a database mapping userid to authentication service identifier that supports user authentication by subsequently accessed applications (e.g., application 230). Manager 250 responds with command status indicator SMResult 707. SMResult 707 indicates command success, failure, not found or time-out in a similar fashion to that previously described in connection with command 237, for example.

A participant child application uses the bidirectional command and response data of FIG. 8 to retrieve a valid userid for this particular child application and for an associated authentication database from the manager 250. A child application (e.g., application 230 of FIG. 2) sends session identifier 800 and authserver (authentication service identifier) 803 (FIG. 8) to manager 250. Manager 250 responds to application 230 with userid 806 valid for the corresponding Authserver 803 used by application 230 and also returns command status indicator SMResult 809. SMResult 809 indicates command success, failure, not found or time-out in a similar fashion to that previously described in connection with command 237, for example. Child application 230 may also employ the authenticating system ID and user ID provided by parent application 200 for validation purposes since these properties are stored by manager 250 in its database. Application 230 obtains the appropriate userid 806 to be used with its authentication service (identified by item 803) to enable access to a user without the need for a user to re-login. This involves participant application 230 relying on previous authentication of the user by parent application 200. In an alternative embodiment, application 230 authenticates the user using a separate authentication process which may be the same or different to the service employed by application 200.

The data format employed for the authserver identifier 803 is configurable within a participant application but ideally conforms to a standard among the participant applications in order to minimize proliferation of different identifiers for a common user within the manager 250 database mapping.

FIG. 16 is a system protocol diagram indicating the hierarchical organization of communication protocol layers used by applications 200 and 230 for communication with browser 10 and manager 250 (FIG. 2). Applications 200 and 230 together with browser 10 and manager 250 provide access to medical information and related services in a system including a communication platform supporting Internet operation and local intra-net operation. The system may also involve other networks including Local Area Networks (LANs), Wide Area Networks (WANs) and other dedicated hospital networks or other medical (or other) systems and communication networks.

An application (e.g., applications 200 and 230) residing in web application layer 984 communicates with manager 250 using a User Interface Interoperability Protocol (UIIP) data format 975 comprising command data structures presented in FIGS. 5–15. The UIIP command and response data 975 involves the TCP/IP (Transmission Control Protocol/Internet Protocol) layer 971. Applications 200 and 230 use the UIIP 975 and TCP/IP 971 layers in communicating with manager 250 in commands 222, 224, 226, 233, 237, 247 and 255 as illustrated in FIG. 2. Manager 250 also communicates with applications 200 and 230 using HTTP and TCP/IP protocol as exemplified in command 257 of FIG. 2. Browser 10 and applications 200 and 230 communicate using (TCP/IP and) HTTP format URL data strings processed in accordance with the UIIP as previously explained and indicated on FIG. 2.

The architectures and processes presented in FIG. 2, FIG. 4 and FIG. 16 are not exclusive and the data formats of FIGS. 5–15 are also adaptable to accommodate different elements and properties. Other architectures and processes may also be derived in accordance with the principles of the invention to accomplish the same objectives. Further, the communication processes and steps of FIG. 2 and data formats of FIGS. 5–15 may be implemented on different platforms for different functions and may be applied within the applications internal to a processing device such as a PC or other processing device or system. The communication processes and data formats may also be applied for Internet or intra-net (or any other network) based work flow or task implementation. The inventive principles may be employed in any system involving the concurrent operation of different applications.

What is claimed is:

1. A system used by a first application for managing user access to at least one of a plurality of network compatible applications, comprising:
   an authentication processor for,
      receiving user identification information including a user identifier and
      initiating authentication of said user identification information using an authentication service; and
   at least one communication processor for,
      communicating an authentication service identifier and a corresponding user identifier to a managing application, said authentication service identifier identifying an authentication service used to authenticate identification information of said corresponding user and automatically communicating application specific context information in a data field of a URL separately from session identification information, to a second application of said plurality of network compatible applications in response to a user command to initiate execution of said second application and in response to authentication of said user identification information, said application specific context information supporting acquisition from said second application of information associated with a current operational context of said first application.

2. A system used by a first application for managing user access to at least one of a plurality of network compatible applications, comprising:

an authentication processor for, receiving user identification information including a user identifier and initiating authentication of said user identification information using an authentication service; and at least one communication processor for, communicating an authentication service identifier and a corresponding user identifier to a managing application, said authentication service identifier identifying an authentication service used to authenticate identification information of said corresponding user and automatically communicating application specific context information in a data field of a URL to a second application of said plurality of network compatible applications in response to a user command to initiate execution of said second application and in response to authentication of said user identification information wherein said application specific context information comprises at least one of, (a) a user identifier and (b) a patient identifier and a communication processor of said at least one communication processor encrypts an address portion of said URL and incorporates said encrypted address portion of said URL, together with said address portion of said URL in non-encrypted form, into a single processed URL data string.

3. A system according to claim 1, wherein said application specific context information comprises a patient identifier, a communication processor of said at least one communication rocessor also communicates a session identifier identifying a user initiated session of operation of said first application to said managing application and said user identification information includes a password associated with said user identifier.

4. A system according to claim 1, wherein a communication processor of said at least one communication processor communicates said authentication service identifier and said corresponding user identifier to a managing application for compilation of a database.

5. A system according to claim 4, wherein said database is accessible by other applications of said plurality of network compatible applications for mapping a non-authenticated user identifier of a participant application to an authenticated and different user identifier of another application.

6. A system used for processing user access to network compatible applications, comprising:

an authentication processor for, receiving authentication service identifier and corresponding user identifier data pairs from at least one of a plurality of applications, compiling a database using said data pairs, mapping a non-authenticated user identifier of a second application to an authenticated different user identifier of a first application using said database; and at least one communication processor for, communicating said authenticated different user identifier to said second application and automatically communicating application specific context information in a data field of a URL separately from session identification information, to said second application in response to a user command to initiate execution of said second application, said application specific context information supporting acquisition from said second application of information associated with a current operational context of said first application.

7. A system according to claim 6, wherein said authentication service identifier identifies an authentication service used to authenticate identification information comprising a user identifier of said corresponding user to provide an authenticated user identifier.

8. A system according to claim 6, wherein said authentication processor performs said mapping using said database by matching an authentication service identifier of said second application with an authentication service identifier of said first application and providing said authenticated different user identifier of said first application as a mapped user identifier.

9. A system according to claim 6, including an input processor for receiving a session identifier identifying a user initiated session of operation wherein said at least one communication processor encrypts an address portion of said URL and incorporates, said encrypted address portion of said URL, together with said address portion of said URL in non-encrypted form, into a single processed URL data string and provides a key supporting decryption of said encrypted address portion to a destination system.

10. A system according to claim 6, wherein said first application is a parent application and said second application is a child application and said authenticated different user identifier of said first application is used by said second application eliminating the need for said second application to authenticate a user identifier.

11. A system according to claim 6, wherein a communication processor of said at least one communication processor communicates a parameter to said second application, said parameter identifying success or failure of said mapping.

12. A system according to claim 6, wherein said authentication processor receives an authentication service identifier and corresponding user identifier data pair from said first application and said first application is a parent application and said second application is a child application.

13. A system according to claim 6, wherein said authentication service identifier employs a predetermined data format for use by said plurality of applications in constraining size of said database.

14. A system used for processing user access to Internet compatible applications, comprising:
an authentication processor for,
receiving an authentication service identifier and corresponding user identifier from a parent application, and
mapping a non-authenticated user identifier of a child application to an authenticated different user identifier of said parent application; and
at least one communication processor for,
communicating said authenticated different user identifier to said child application and
automatically communicating application specific context information in a data field of a URL separately from session identification information, to said child application in response to a user command to initiate execution of said child application and in response to communicating said authenticated different user identifier, said application specific context information supporting acquisition from said child application of information associated with a current operational context of said parent application.

15. A system according to claim 14, wherein
said parent application establishes a session of user operation and
said child application uses said authentication system to participate in said session of user operation.

16. A system according to claim 14, wherein
said authentication processor compiles a database using data pairs comprising an authentication service identifier and corresponding user identifier and a data pair is received from individual applications of a plurality of concurrently operating Internet compatible applications and
said authentication processor uses said database in mapping said non-authenticated user identifier of said child application to said authenticated different user identifier of said parent application.

17. A system according to claim 16, wherein
said authentication, processor performs said mapping using said database by matching an authentication service identifier of said child application with an authentication service identifier of said parent application and providing said authenticated different user identifier of said parent application as a mapped user identifier.

18. A system according to claim 14, wherein
said authentication service identifier identifies an authentication service used to authenticate identification information comprising a user identifier of said corresponding user to provide an authenticated user identifier.

19. A system according to claim 14, wherein
said application specific context information comprises a patient identifier and
said authenticated different user identifier of said parent application is used by said child application eliminating the need for said child application to authenticate a user identifier.

20. A system according to claim 14, wherein
access to said child application by a user is enabled by said child application in response to receiving said authenticated different user identifier without a subsequent re-entry of user identification information via a logon menu.

21. A method used for processing user access to Internet compatible applications, comprising the activities of:
receiving an authentication service identifier and corresponding user identifier from a parent application, and
mapping a non-authenticated user identifier of a child application to an authenticated different user identifier of said parent application;
communicating said authenticated different user identifier to said child application; and
automatically communicating application specific context information in a data field of a URL separately from session identification information, to said child application in response to a user command to initiate execution of said child application and in response to communicating said authenticated different user identifier, said application specific context information supporting acquisition from said child application of information associated with a current operational context of said parent application.

22. A method according to claim 21, including the activities of
receiving data pairs, comprising an authentication service identifier and corresponding user identifier, from individual applications of a plurality of concurrently operating Internet compatible applications,
compiling a database using said data pairs, and
using said database in mapping said non-authenticated user identifier of said child application to said authenticated different user identifier of said parent application.

23. A method used by a first application for managing user access to at least one of a plurality of network compatible applications, comprising the activities of:
receiving user identification information including a user identifier;
initiating authentication of said user identification information using an authentication service;
communicating an authentication service identifier and a corresponding user identifier to a managing application, said authentication service identifier identifying an authentication service used to authenticate identification information of said corresponding user; and
automatically communicating application specific context information in a data field of a URL separately from session identification information, to a second application of said plurality of network compatible applications in response to a user command to initiate execution of said second application and in response to authentication of said user identification information, said application specific context information supporting acquisition from said second application of information associated with a current operational context of said first application.

* * * * *